US012573036B2

(12) United States Patent
Wilson et al.

(10) Patent No.: US 12,573,036 B2
(45) Date of Patent: Mar. 10, 2026

(54) PREDICTION OF MAJOR ADVERSE CARDIOVASCULAR EVENTS (MACE) FROM AI ANALYSIS OF PERICORONARY FAT IN CT IMAGES

(71) Applicants: Case Western Reserve University, Cleveland, OH (US); University Hospitals Cleveland Medical Center, Cleveland, OH (US)

(72) Inventors: David L. Wilson, Cleveland Heights, OH (US); Ammar Hoori, Westlake, OH (US); Tao Hu, Cleveland, OH (US); Yingnan Song, Cleveland, OH (US); Hao Wu, Cleveland, OH (US); Juhwan Lee, Westlake, OH (US); Sadeer Al-Kindi, Cleveland, OH (US); Sanjay Rajagopalan, Cleveland, OH (US)

(73) Assignees: Case Western Reserve University, Cleveland, OH (US); University Hospitals Cleveland Medical Center, Cleveland, OH (US)

( * ) Notice: Subject to any disclaimer, the term of this patent is extended or adjusted under 35 U.S.C. 154(b) by 302 days.

(21) Appl. No.: 18/354,921

(22) Filed: Jul. 19, 2023

(65) Prior Publication Data

US 2024/0169525 A1    May 23, 2024

Related U.S. Application Data

(60) Provisional application No. 63/427,143, filed on Nov. 22, 2022.

(51) Int. Cl.
*G06T 7/00* (2017.01)
*G06T 7/11* (2017.01)
(Continued)

(52) U.S. Cl.
CPC .............. *G06T 7/0012* (2013.01); *G06T 7/11* (2017.01); *G06T 7/30* (2017.01); *G06V 10/26* (2022.01);
(Continued)

(58) Field of Classification Search
CPC ..................................................... G06V 20/50
See application file for complete search history.

(56) References Cited

U.S. PATENT DOCUMENTS 11,393,137 B2 *    7/2022    Antoniades ............ A61B 6/032
2018/0051340 A1 *   2/2018    Helgason ................ A61P 35/00
(Continued)

*Primary Examiner* — Edward Park
(74) *Attorney, Agent, or Firm* — Eschweiler & Potashnik, LLC

(57) ABSTRACT

The present disclosure, in some embodiments, relates to a method of generating a prognosis for a patient. The method includes accessing automatically segmented pericoronary adipose tissue (PCAT) corresponding to a patient within an electronic memory. A plurality of non-confounding PCAT features are generated by measuring values of Hounsfield units for an imaging unit within the PCAT. The measured values of the Hounsfield units are predominately free of iodine confounding and artifacts. The plurality of non-confounding PCAT features are provided to a regression model. The regression model is configured to generate a prognosis for the patient using the plurality of non-confounding PCAT features

17 Claims, 12 Drawing Sheets

(51) Int. Cl.

| | |
|---|---|
| *G06T 7/30* | (2017.01) |
| *G06V 10/26* | (2022.01) |
| *G06V 10/44* | (2022.01) |
| *G06V 10/766* | (2022.01) |
| *G06V 10/774* | (2022.01) |
| *G06V 20/50* | (2022.01) |
| *G16H 50/30* | (2018.01) |
| *G16H 50/70* | (2018.01) |

(52) U.S. Cl.
CPC ............ *G06V 10/44* (2022.01); *G06V 10/766* (2022.01); *G06V 10/774* (2022.01); *G06V 20/50* (2022.01); *G16H 50/30* (2018.01); *G16H 50/70* (2018.01); *G06T 2207/10081* (2013.01); *G06T 2207/20081* (2013.01); *G06T 2207/30048* (2013.01); *G06V 2201/031* (2022.01)

(56)                          References Cited

U.S. PATENT DOCUMENTS

| | | | |
|---|---|---|---|
| 2019/0249257 A1* | 8/2019 | Ching | C12Q 1/6886 |
| 2020/0226749 A1* | 7/2020 | Freiman | A61B 6/5217 |
| 2024/0169525 A1* | 5/2024 | Wilson | G06V 10/26 |

\* cited by examiner

100 —

200

300 →

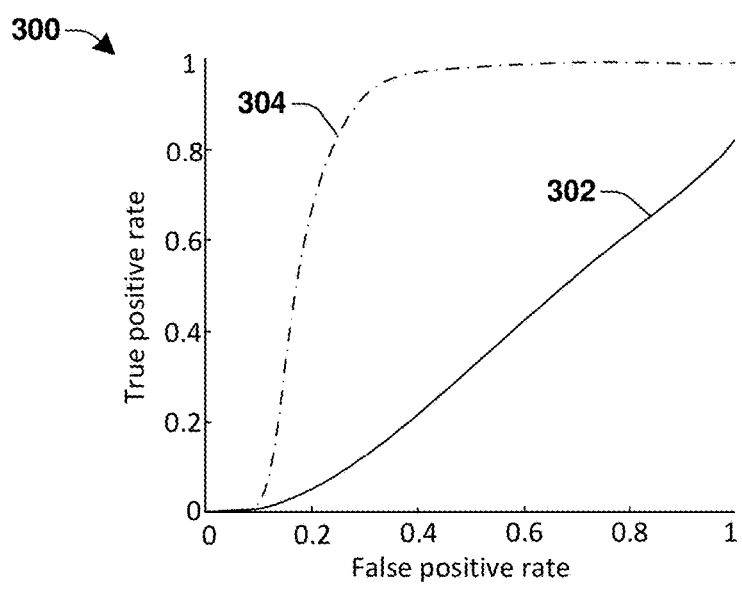

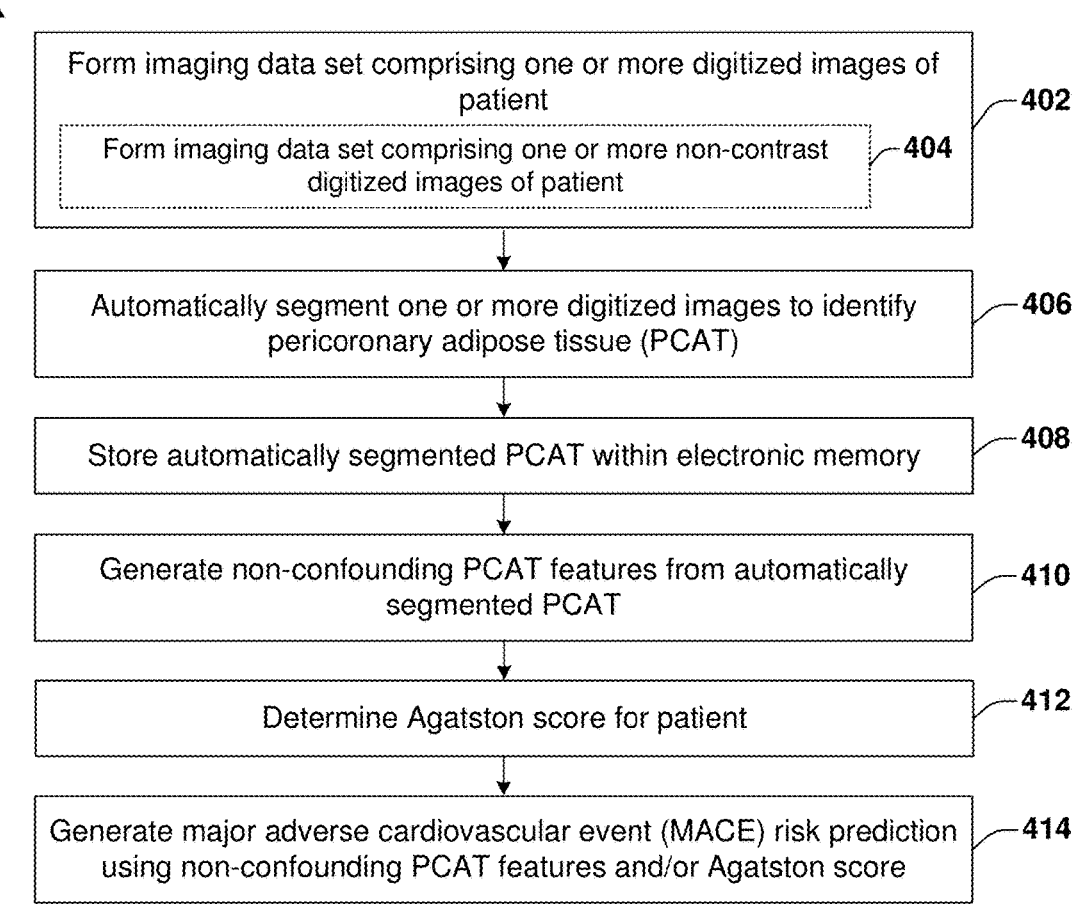

| Form imaging data set comprising one or more digitized images of patient | ⌐402 |
|---|---|
| Form imaging data set comprising one or more non-contrast digitized images of patient ⌐404 | |

Automatically segment one or more digitized images to identify pericoronary adipose tissue (PCAT)    ⌐406

Store automatically segmented PCAT within electronic memory    ⌐408

Generate non-confounding PCAT features from automatically segmented PCAT    ⌐410

Determine Agatston score for patient    ⌐412

Generate major adverse cardiovascular event (MACE) risk prediction using non-confounding PCAT features and/or Agatston score    ⌐414

600 ⬎
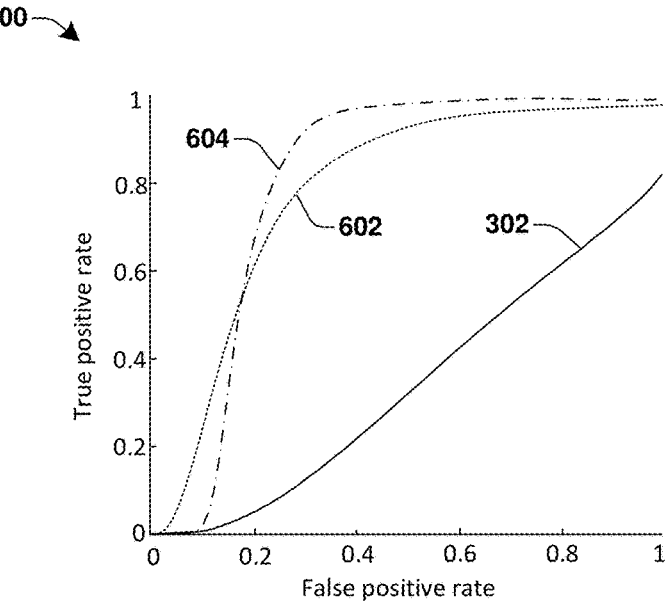
Fig. 6
700 ⬎        706 ⬎
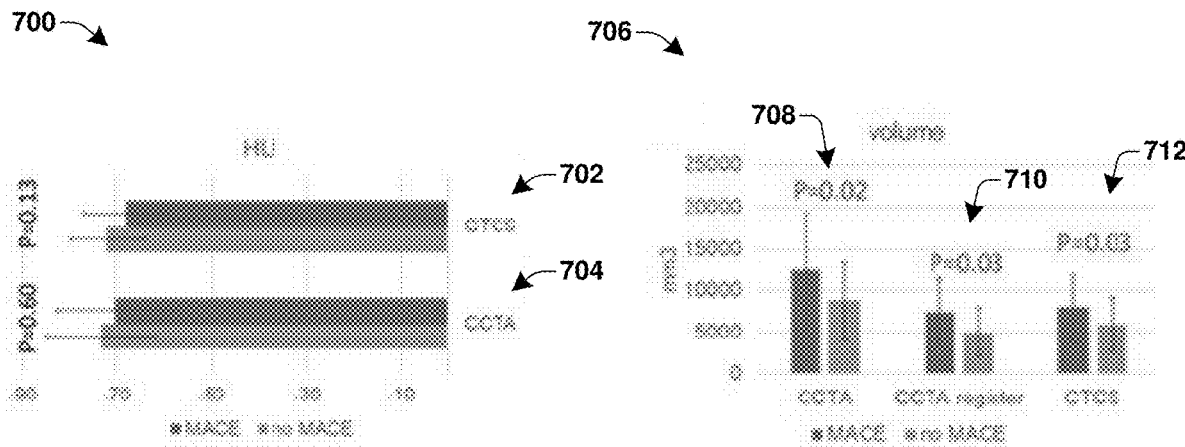
Fig. 7A                          Fig. 7B

1000

1100

1200

1300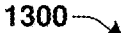

Form imaging data set comprising one or more CCTA images, CCTP images, and CTCS images of patient /—1302

Process one or more one or more CCTA images and CCTP images
- - - - - - - - - - - - - - - - - - - - - - - - - - - - - - - - - - - - - - - -
| Perform automated beam hardening correction | /—1306
- - - - - - - - - - - - - - - - - - - - - - - - - - - - - - - - - - - - - - - -
| Perform 3D registration to minimize motion between image frames | /—1308
- - - - - - - - - - - - - - - - - - - - - - - - - - - - - - - - - - - - - - - -
| Perform partial scan artifact reduction | /—1310
- - - - - - - - - - - - - - - - - - - - - - - - - - - - - - - - - - - - - - - -
| Perform spatio temporal bilateral filtering | /—1312
- - - - - - - - - - - - - - - - - - - - - - - - - - - - - - - - - - - - - - - -
/—1304

Segment one or more CCTA images, CCTP images, and CTCS images to identify pericoronary adipose tissue (PCAT) /—1314

Store automatically segmented PCAT within electronic memory /—1316

Compute perfusion blood flow in PCAT of CCTP images /—1318

Assess blood flow and/or iodine perfusion in PCAT of CCTP images using PCAT blood flow /—1320

Extract PCAT features from PCAT of CCTA images taking into account blood flow and/or iodine perfusion /—1322

Extract Non-confounded PCAT features from automatically segmented PCAT of CTCS images using PCAT features extracted from PCAT of CCTA images /—1324

Determine Agatston score associated with patient /—1326

Generate major adverse cardiovascular event (MACE) risk prediction using extracted PCAT features and/or Agatston score /—1328

Fig. 13

PREDICTION OF MAJOR ADVERSE CARDIOVASCULAR EVENTS (MACE) FROM AI ANALYSIS OF PERICORONARY FAT IN CT IMAGES

CROSS REFERENCE TO RELATED APPLICATIONS

This application claims the benefit of priority from U.S. Provisional Patent Application No. 63/427,143 filed Nov. 22, 2022 and entitled "PREDICTION OF MAJOR ADVERSE CARDIOVASCULAR EVENTS (MACE) FROM AI ANALYSIS OF PERICORONARY FAT IN CT IMAGES", the contents of which are incorporated herein by reference in their entirety.

BACKGROUND

The heart pumps blood with oxygen and nutrients to different parts of the human body through a network of blood vessels. The heart is the primary organ of the circulatory system and is essential for human life. Atherosclerotic blood vessel disease can lead to events such as strokes, myocardial infractions, and/or even death.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 3 illustrates an exemplary receiver operating characteristic (ROC) curve comparing a disclosed method for MACE prediction with other methods for MACE prediction.

FIG. 4 illustrates a flow diagram corresponding to some embodiments of a method of determining a likelihood of a MACE using non-confounding PCAT features.

FIG. 6 illustrates an exemplary ROC curve comparing a disclosed method for MACE prediction with other methods for MACE prediction.

FIG. 7A illustrates a graph showing some exemplary Hounsfield unit (HU) values for a patient with a MACE and for a patient without a MACE.

FIG. 7B illustrates a graph showing some exemplary PCAT volumes for a patient with a MACE and for a patient without a MACE.

FIG. 13 illustrates a flow diagram corresponding to some additional embodiments of a method of determining a likelihood of a MACE using non-confounding PCAT features.

DETAILED DESCRIPTION

Figure 1:
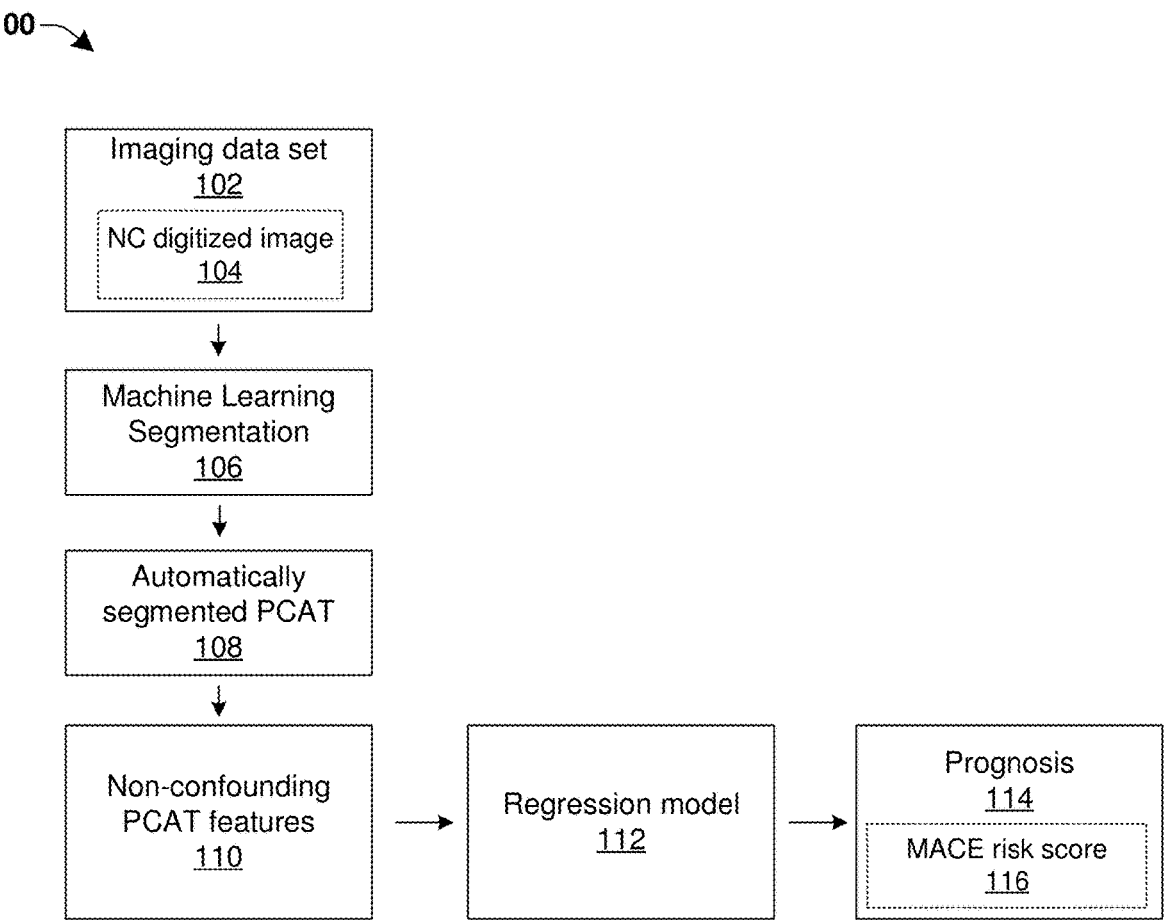
FIG. 1 illustrates a block diagram corresponding to some embodiments of an assessment apparatus configured to determine a prognosis based off of non-confounding features extracted from pericoronary adipose tissue (PCAT).

The description herein is made with reference to the drawings, wherein like reference numerals are generally utilized to refer to like elements throughout, and wherein the various structures are not necessarily drawn to scale. In the following description, for purposes of explanation, numerous specific details are set forth in order to facilitate understanding. It may be evident, however, to one of ordinary skill in the art, that one or more aspects described herein may be practiced with a lesser degree of these specific details. In other instances, known structures and devices are shown in block diagram form to facilitate understanding.

Cardiovascular disease is the most common cause of death in the United States. Among the many factors (e.g., C-reactive protein and family history) that may be indicative of cardiovascular disease within a patient, an Agatston score is often considered to be one of the most indictive. An Agatston score is a score that correlates to an extent of coronary artery calcification detected by an unenhanced low-dose CT scan. High risk plaque (HRP) characteristics (e.g., low-attenuation plaque, napkin ring sign, positive remodeling, and spotty plaque calcification) extracted from coronary computed tomography angiogram (CCTA) images are also indicative of cardiovascular disease. However, many patients that are classified as high risk using an Agatston score and/or CCTA HRP characteristics do not suffer a major adverse cardiovascular event (MACE), while other patients that are classified as low risk using an Agatston score and/or CCTA HRP characteristics do suffer a MACE, thereby indicating an opportunity for improvement of current prognostic techniques.

Artificial intelligence (AI) and statistical models based upon various clinical assessments can also be used forecast a MACE, providing information for personalized medicine. Among currently accepted clinical assessments (e.g., body mass index), detection and quantification of coronary artery calcium (CAC) in computed tomography calcium score exams (CTCS) may be used as a powerful biomarker for the prediction of MACE. Recently, there has been a notable focus on pericoronary adipose tissue (PCAT) as assessed in coronary computed tomography angiography (CCTA) images as a risk factor for MACE A human heart has a wall containing three different layers: the endocardium (e.g., inner layer), the myocardium (muscular middle layer), and the epicardium (e.g., protective outer layer). The epicardium is one layer of the pericardium, a protective sac that surrounds the entire heart. Pericoronary adipose tissue (PCAT) (e.g., pericoronary fat or epicardial fat) is body fat that is located between surfaces of the myocardium and the epicardium. PCAT may also directly surround main coronary arteries. It has been appreciated that inflammation of PCAT may be a contributing factor to coronary artery disease. For example, inflammatory cells (e.g., hematopoietic cells, adipocytes) within PCAT may be delivered to a coronary artery and/or to plaque within a coronary artery by vasa vasorum (e.g., small blood vessels that extend between an artery and an outermost wall of the artery) and may influence atherosclerosis plaque progression (e.g., contributing to plaque inflammation) by contributing to the development of atherosclerotic cardiovascular disease events (e.g., atherosclerosis) via production of adipocytokines (leptin, MCP-1, TNFα, etc.). Therefore, inflammatory mechanisms in a vascular wall and/or PCAT may influence residual risk for atherosclerotic cardiovascular disease events.

With inflammation, PCAT tissue properties change. These changes can be detected by measurement of CT Hounsfield unit (HU) values in a 3D distribution of tissue around a coronary artery using CCTA. Therefore, CT imaging of PCAT may be a promising measure of inflammation and atherosclerosis that can improve risk prediction. For example, fat attenuation index (FAI), which is defined as a mean pericoronary fat HU within a radial distance from an outer coronary wall equal to the average vessel diameter, may be associated with morphological changes in PCAT due to inflammation and the presence of coronary artery disease.

Current assessments of PCAT, while predictive, use post-contrast CCTA images. However, it has been appreciated that iodine confoundment (e.g., from varying iodine enhancement due to uneven timing of CCTA acquisitions and to the presence of obstructive disease, which delays and reduces enhancement) in post-contrast CCTA may affect values of HU within an image. The affected values may lead to elevated fat attenuation index (FAI) and/or affect texture radiomics related to vascular filling of iodine, thereby reducing an ability of machine learning models to predict major adverse cardiovascular events (MACE) using PCAT features. Therefore, the confounding presence of iodine (e.g., especially regarding average HU values and the size of the PCAT volume) can decrease a reliability of such assessments. The present disclosure allows a health care provider to assess PCAT using a low-cost or no-cost CTCS image without the confound of iodine in CCTA images.

The present disclosure, in some embodiments, relates to a method and associated apparatus that utilizes non-confounding PCAT features extracted from pericoronary adipose tissue (PCAT) within digitized images (e.g., low-dose computed tomography (CT) calcium score (CTCS) images) to predict major adverse cardiovascular events (MACE). In some embodiments, the method comprises accessing segmented image data that identifies pericoronary adipose tissue (PCAT) from one or more digitized images. A plurality of non-confounding PCAT features, which are predominantly free of iodine confounding, are generated from the PCAT and provided to a regression model. The regression model is configured to generate a major adverse cardiovascular event (MACE) risk score using the plurality of non-confounding PCAT features. By using non-confounding PCAT features that are predominantly free of iodine confounding, Hounsfield unit (HU) values of PCAT can be more accurately measured and a more accurate prediction of MACE can be achieved.

FIG. 1 illustrates a block diagram corresponding to some embodiments of an assessment apparatus 100 configured to determine a prognosis based off of non-confounding features extracted from pericoronary adipose tissue (PCAT).

The assessment apparatus 100 comprises a machine learning segmentation tool 106 that is configured to access one or more digitized images within an imaging data set 102. In some embodiments, the one or more non-contrast digitized images may comprise cardiovascular computed tomography (CT) images. For example, in various embodiments the one or more non-contrast digitized images may comprise non-contrast, fast, low-dose computed tomography calcium score (CTCS) images, images of the chest (e.g., lung screening images), or the like. In some embodiments, the one or more non-contrast digitized images may be EKG (electro-cardiogram) gated.

The machine learning segmentation tool 106 is configured to segment the one or more digitized images 104 to generate one or more automatically segmented images that identify automatically segmented pericoronary adipose tissue (PCAT) 108 within the one or more digitized images 104.

A plurality of non-confounding PCAT features 110 are generated from the automatically segmented PCAT 108. The plurality of non-confounding PCAT features 110 are features relating to the automatically segmented PCAT 108 that are predominantly free of confounding from iodine (e.g., that are substantially free or completely free of confounding from iodine). In some embodiments, one or more of the plurality of non-confounding PCAT features 110 may be determined by measuring a Hounsfield Unit (HU) value of an imaging unit (e.g., a pixel or a voxel) of the automatically segmented PCAT 108. Because the plurality of non-confounding PCAT features 110 are predominantly free of confounding from iodine, the plurality of non-confounding PCAT features 110 can be generated with accurate HU values. In various embodiments, the plurality of non-confounding PCAT features 110 may comprise intensity features, morphology features, and texture features.

The plurality of non-confounding PCAT features 110 are provided to a regression model 112 that is configured to utilize the plurality of non-confounding PCAT features 110 to generate a prognosis 114. In some embodiments, the prognosis 114 may comprise a MACE risk score 116 that is indicative of a likelihood that a patient will have a major adverse cardiovascular event (MACE) (e.g., cardiovascular death, myocardial infarction, hospitalization for unstable angina, and late revascularization, including percutaneous coronary intervention and coronary bypass graft). In other embodiments, the prognosis 114 may comprise a prediction of atherosclerosis and/or future coronary calcifications. In yet other embodiments, the prognosis 114 may comprise a prediction relating to health disparities, genes, cardiometabolic risk, co-morbidities (e.g., diabetes), cardio-oncology, and/or the like.

It has been appreciated that measurement of PCAT features may be influenced by the presence of iodine in the PCAT. For example, the presence of iodine in the automatically segmented PCAT 108 will increase HU value leading to elevated FAI, affecting texture radiomics related to vascular filling of iodine, etc. However, by generating the plurality of non-confounding PCAT features 110 to be predominantly free of confounding from iodine, the disclosed assessment apparatus 100 is able to provide the prognosis 114 (e.g., prediction of a MACE) with a high degree of accuracy.

Figure 2:
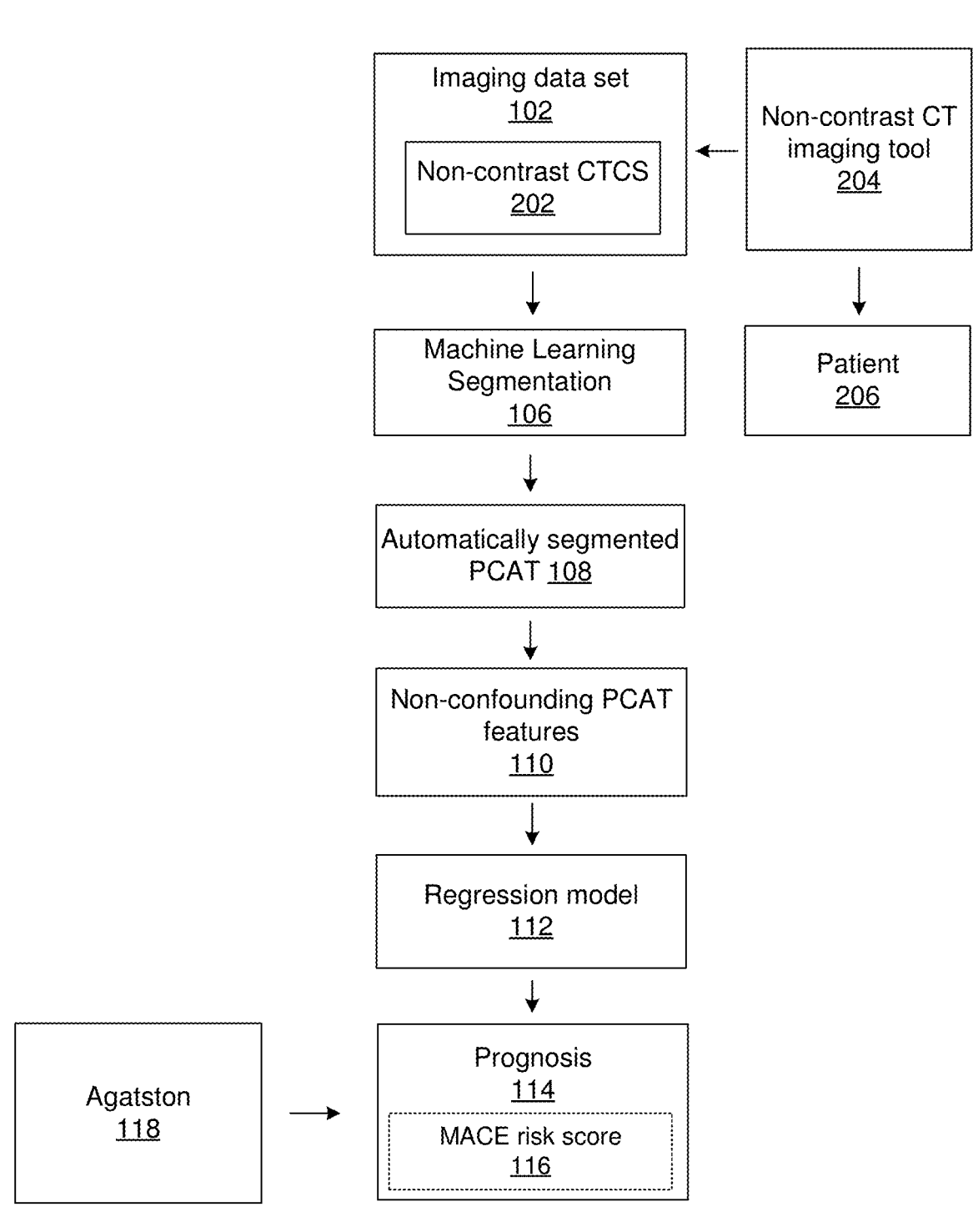
FIG. 2 illustrates a block diagram corresponding to some additional embodiments of an assessment apparatus configured to determine a prognosis using non-confounding PCAT features.

FIG. 2 illustrates a block diagram corresponding to some additional embodiments of an assessment apparatus 200 configured to determine a prognosis based off of non-confounding features extracted from pericoronary adipose tissue (PCAT).

The assessment apparatus 200 comprises an imaging data set 102 comprising one or more non-contrast computed tomography calcium score (CTCS) images 202 (e.g., one or more low-dose CTCS images). The one or more non-contrast CTCS images 202 are substantially free of confounding and/or artifacts due to the presence of iodine within imaged tissue and thus allow for non-confounding features to be easily extracted. Therefore, the one or more non-contrast CTCS images 202 offer a low-cost screening assessment that avoids iodine confoundment to lead to more accurate PCAT features and a more accurate prediction of MACE. In some embodiments, the imaging data set 102 may be formed by operating a non-contrast CT imaging tool 204 on a patient 206. In some embodiments, the non-contrast CT imaging tool 204 may comprise a low-dose non-contrast computed tomography (CT) scanner. In some embodiments, the patient 206 may have and/or may be suspected of having cardiovascular disease.

A machine learning segmentation tool 106 is configured to segment the one or more non-contrast CTCS images 202 to generate one or more automatically segmented images that identify automatically segmented pericoronary adipose tissue (PCAT) 108 within the non-contrast CTCS images 202. In some embodiments, the machine learning segmentation tool 106 may comprise a deep learning model. In some embodiments, the machine learning segmentation tool 106 may be configured to segment the one or more non-contrast CTCS images 202 to identify coronary arteries of a heart and the automatically segmented PCAT 108 surrounding the coronary arteries. In some embodiments, the automatically segmented PCAT 108 may be stored within electronic memory.

A plurality of non-confounding PCAT features 110 are extracted from the automatically segmented PCAT 108. The plurality of non-confounding PCAT features 110 are features relating to the automatically segmented PCAT 108 and that are predominantly free of confounding from iodine. In various embodiments, the plurality of non-confounding PCAT features 110 may comprise intensity features, morphology features, and texture features.

The plurality of non-confounding PCAT features 110 are provided to a regression model 112 that is configured to utilize the plurality of non-confounding PCAT features 110 to generate a prognosis 114. In some embodiments, the prognosis 114 may comprise a major adverse cardiovascular event (MACE) risk score 116 that is indicative of a likelihood that a patient will have a MACE (e.g., cardiovascular death, myocardial infarction, hospitalization for unstable angina, and late revascularization (including percutaneous coronary intervention and coronary bypass graft)). In some embodiments, the regression model 112 may comprise a Cox-proportional hazard time-to-event model.

In some embodiments, the MACE risk score 116 may be determined by further taking into consideration an Agatston score 118, so that the MACE risk score 116 is based upon both the plurality of non-confounding PCAT features 110 and the Agatston score 118. Taking into consideration the Agatston score 118, in addition to the plurality of non-confounding PCAT features 110, may improve an accuracy of the MACE risk score 116. For example, a multivariate logistic regression model operated upon a combination of the plurality of non-confounding PCAT features 110 and the Agatston score 118 may generate results (e.g., an AUC=0.80) that far exceed that for the Agatston score 118 alone.

FIG. 3 illustrates an exemplary receiver operating characteristic (ROC) curve 300 comparing a disclosed method for MACE prediction with other methods for MACE prediction. The ROC curve 300 plots a true positive rate (TPR) along the y-axis and a false positive rate (FPR) along the x-axis.

The ROC curve 300 includes a first curve 302 corresponding to MACE prediction based upon an Agatston score and a second curve 304 corresponding to MACE prediction based upon a combination of an Agatston score and a plurality of non-confounding PCAT features extracted from one or more digitized images. As can be seen by comparison of the first curve 302 with the second curve 304, the inclusion of the plurality of non-confounding PCAT features significantly improves area under curves (AUCs).

FIG. 4 illustrates a flow diagram corresponding to some embodiments of a method 400 of determining a likelihood of a MACE using non-confounding PCAT features.

While the disclosed methods (e.g., methods 400 and 1300) are illustrated and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At act 402, an imaging data set is formed to comprise one or more digitized images of a patient. In some embodiments, the imaging data set may be formed to comprise one or more non-contrast digitized images at act 404. In some such embodiments, the imaging data set may be formed by performing one or more non contrast radiological imaging procedures on the patient to form the one or more non-contrast digitized images. In some embodiments, the one or more non-contrast digitized images may comprise one or more non-contrast low-dose computed tomography calcium score (CTCS) images.

At act 406, the one or more digitized images are automatically segmented to identify pericoronary adipose tissue (PCAT). In some embodiments, the one or more digitized images may be segmented using a deep learning model.

At act 408, the automatically segmented PCAT is stored in an electronic memory.

At act 410, a plurality of non-confounding PCAT features are generated from the automatically segmented PCAT.

At act 412, an Agatston score is determined for the patient.

At act 414, a major adverse cardiovascular event (MACE) risk prediction is generated using the plurality of non-confounding PCAT features and/or the Agatston score. In some embodiments, the MACE risk prediction may be generated by operating a regression model upon the plurality of non-confounding PCAT features and/or the Agatston score.

Figure 5A:
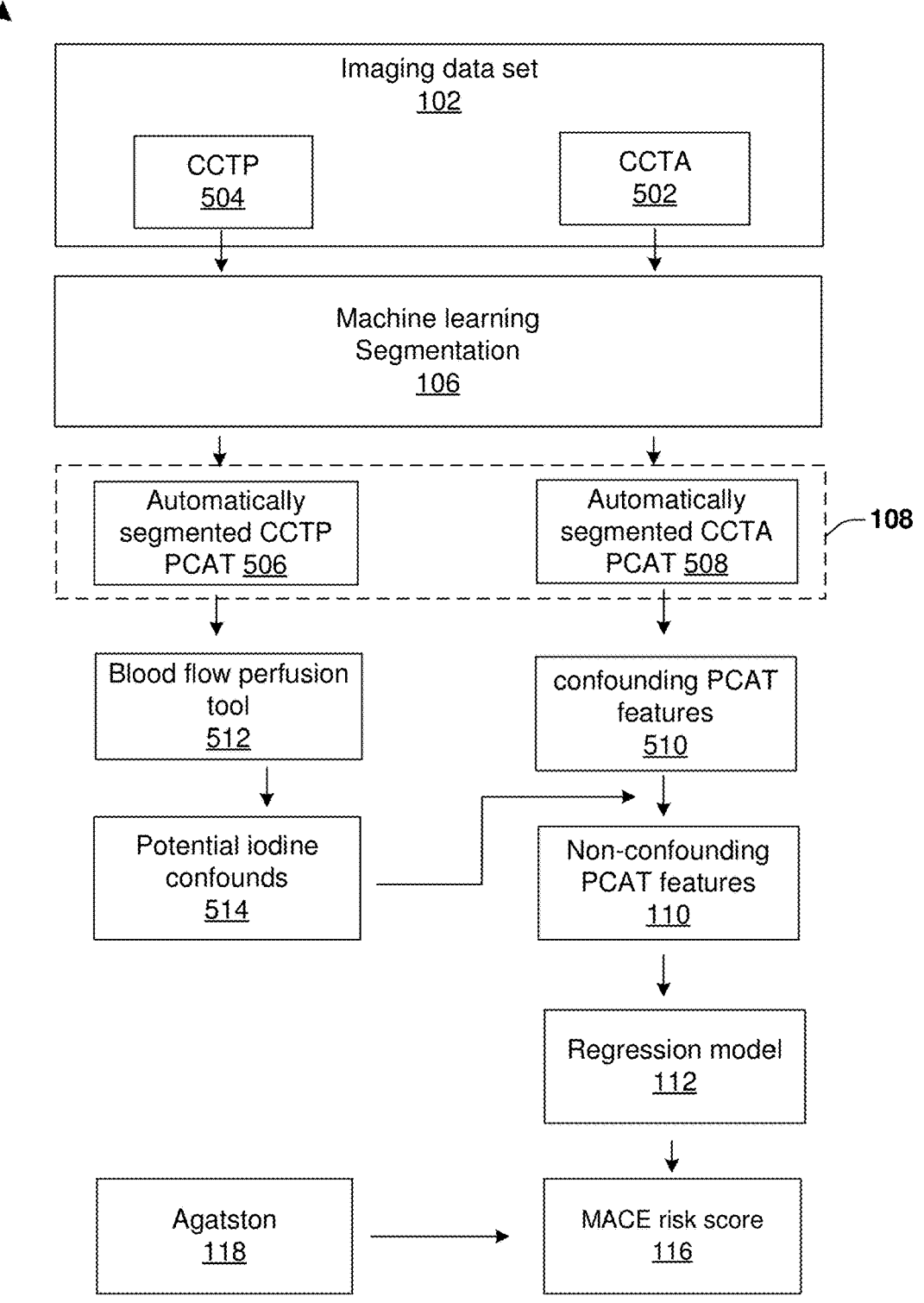
FIG. 5A illustrates a block diagram corresponding to some embodiments of a MACE assessment apparatus configured to determine a likelihood of a MACE using non-confounding PCAT features.

FIG. 5A illustrates a block diagram corresponding to some embodiments of a MACE assessment apparatus 500 configured to determine a likelihood of a MACE using non-confounding PCAT features.

The MACE assessment apparatus 500 comprises an imaging data set 102 comprising one or more digitized images including one or more cardiac computed tomography angiography images (CCTA) images 502 and one or more cardiac CT perfusion images (CCTP) images 504. A machine learning segmentation tool 106 is configured to access the one or more digitized images within the imaging data set 102. The machine learning segmentation tool 106 is configured to segment the one or more digitized images to identify automatically segmented pericoronary adipose tissue (PCAT) 108 within the one or more digitized images. In some embodiments, the automatically segmented PCAT 108 may comprise automatically segmented CCTP PCAT 506 and automatically segmented CCTA PCAT 508.

A plurality of confounding PCAT features 510 are extracted from the automatically segmented CCTA PCAT 508. In various embodiments, the plurality of confounding PCAT features 510 may comprise intensity features, morphology features, and texture features. In some embodiments, the plurality of confounding PCAT features 510 may be modified to try to account for iodine confounds within the one or more CCTA images 502, resulting in the formation of a plurality of non-confounding PCAT features 110.

The amount of iodine in PCAT will depend in-part upon a time since injection and/or obstructive disease in territories. Therefore, in some embodiments, the automatically segmented CCTP PCAT 506 may be provided to a blood flow perfusion tool 512, which is configured to calculate a blood flow perfusion and to calculate potential iodine confounds 514 from the blood flow perfusion. In some embodiments, the potential iodine confounds 514 (e.g., especially due to obstructive disease) may be calculated by analyzing HU and texture features at various time points in dynamic CCTP images. The potential iodine confounds 514 can be used to modify the plurality of confounding PCAT features 510 to generate the plurality of non-confounding PCAT features 110, which are able to provide a greater accuracy in MACE prediction.

The plurality of non-confounding PCAT features 110 are provided to a regression model 112 that is configured to utilize the plurality of non-confounding PCAT features 110 to generate a MACE risk score 116 that is indicative of a likelihood that a patient will have a MACE. Because the plurality of confounding PCAT features 510 are modified using the potential iodine confounds 514 to generate the plurality of non-confounding PCAT features 110, the disclosed MACE assessment apparatus 500 is able to offer an accurate prediction of MACE.

Figure 5B:
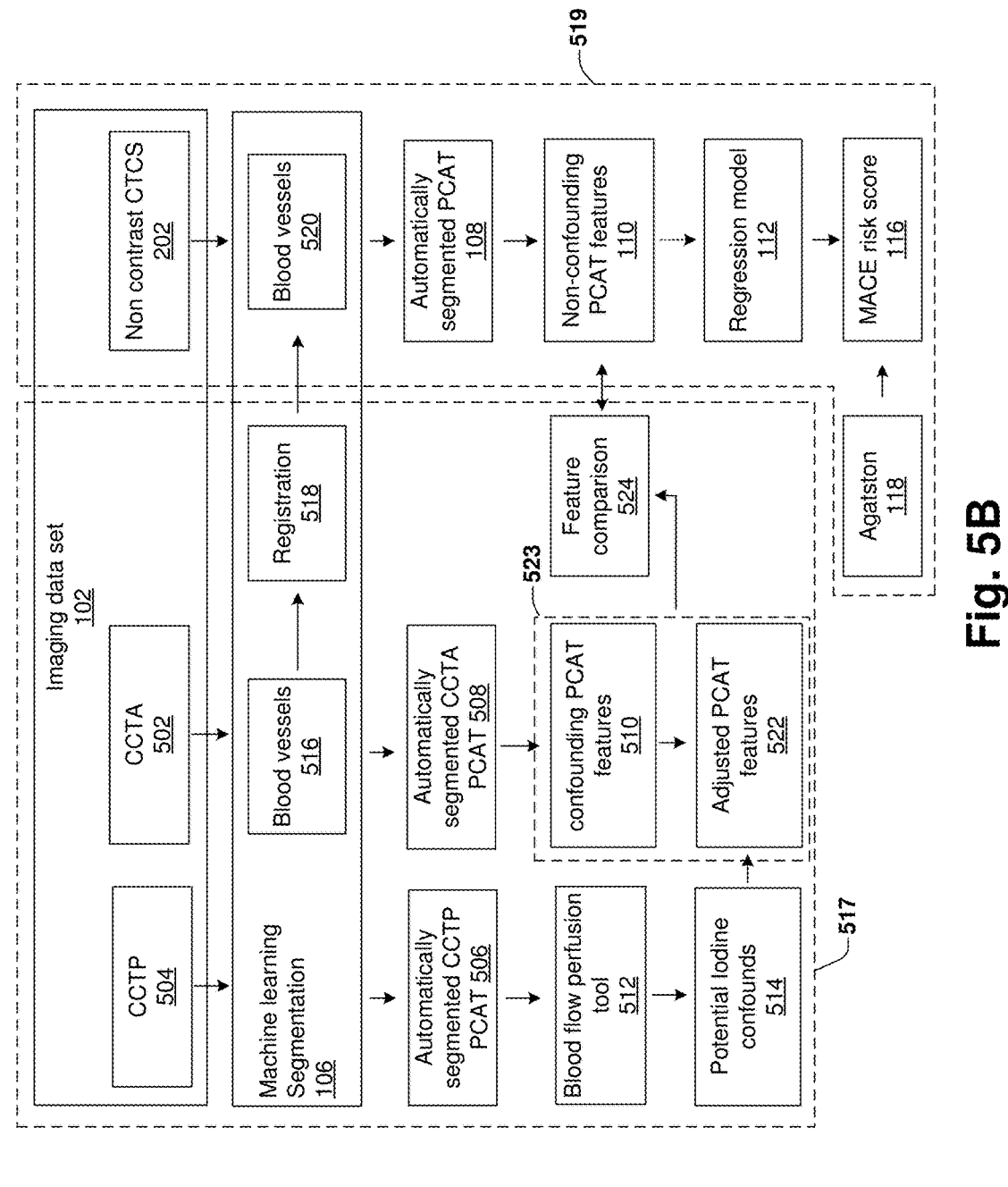
FIG. 5B illustrates a block diagram corresponding to some additional embodiments of a MACE assessment apparatus configured to determine a likelihood of a MACE using non-confounding PCAT features.

FIG. 5B illustrates a block diagram corresponding to some additional embodiments of a MACE assessment apparatus 515 configured to determine a likelihood of a MACE using non-confounding PCAT features.

The MACE assessment apparatus 515 comprises an imaging data set 102 including one or more digitized images. In some embodiments, the imaging data set 102 may comprise one or more non-contrast CTCS images 202. In some additional embodiments, the imaging data set 102 may further comprise one or more CCTA images 502 and one or more CCTP images 504.

The MACE assessment apparatus 515 comprises a training stage 517 and an operating stage 519. The training stage 517 is configured to utilize the one or more CCTA images 502 and/or one or more CCTP images 504 to train the operating stage 519 to accurately extract features from the one or more non-contrast CTCS images 202. It will be appreciated that once training is completed, the training stage 517 may be excluded from the MACE assessment apparatus 500, such that in some embodiments the MACE assessment apparatus 500 consists of the operating stage 519. In such embodiments, the imaging data set 102 may comprise the one or more non-contrast CTCS images 202, but not CCTA images and/or CCTP images.

A machine learning segmentation tool 106 is configured to access one or more digitized images within an imaging data set 102. The machine learning segmentation tool 106 is configured to segment the one or more non-contrast CTCS images 202 to identify automatically segmented pericoronary adipose tissue (PCAT) 108 within the one or more non-contrast CTCS images 202. The machine learning segmentation tool 106 may also be configured to segment the one or more CCTA images 502 to identify automatically segmented CCTA PCAT 508 within the one or more CCTA images 502 and to segment the one or more CCTP images 504 to identify automatically segmented CCTP PCAT 506 within the one or more CCTP images 504.

In some embodiments, the machine learning segmentation tool 106 (e.g., deep learning segmentation model) may be trained to segment the one or more non-contrast CTCS images 202 by using inputs from contrast images (e.g., the one or more CCTA images 502). In some embodiments, PCAT may be identified from the one or more CCTA images 502 using one or more image labels (e.g., blood vessels, coronary type, lumen, centerline, PCAT-cyl-mask, or the like), which are more readily visible in the one or more CCTA images 502 than in the one or more non-contrast CTCS images 202. For example, locations of one or more blood vessels 516 within the one or more CCTA images may be determined and registered 518 with the locations of one or more blood vessels 520 within the one or more non-contrast CTCS images 202 to guide the machine learning segmentation tool 106.

In some embodiments, the one or more CCTA images 502 may be segmented to identify three main coronary arteries (e.g., left anterior descending (LAD), left circumflex artery (LCX), and right coronary artery (RCA)), including vessel centerlines. Since the one or more CCTA images 502 and the one or more non-contrast CTCS images 202 are separately acquired and a patient may not in an identical position during the separate acquisitions, the one or more CCTA images 502 may be registered to the one or more non-contrast CTCS images 202 using non-rigid registration. After registration, labels and centerlines for the main coronary arteries are transformed to corresponding locations in the one or more non-contrast CTCS images 202. The one or more non-contrast CTCS images 202 and transformed labels serve as training and testing data. The machine learning segmentation tool 106 then segments the coronary artery in one or more non-contrast CTCS images 202. In some embodiments, the machine learning segmentation tool 106 may comprise a 3D mask region-based convolutional neural network (R-CNN).

A plurality of non-confounding PCAT features 110 are extracted from the automatically segmented PCAT 108. In some embodiments, the plurality of non-confounding PCAT features 110 may comprise one or more of intensity features, morphology features, and texture features. In some embodiments, the intensity features may include histogram related features such as minimum, mean, standard deviation, median, maximum value, skewness, kurtosis, entropy, potentially large bin histograms within fat region, and/or the like. In some embodiments, the morphology features may include volume, shape, extent, and/or the like. In some embodiments, the texture features may include Gray-Level Co-Occurrence Matrix (GLCM), Gray Level Dependence Matrix (GLDM), Gray Level Run Length Matrix (GLRLM), and Neighborhood Grey-Tone Difference Matrix (NGTDM), and/or the like. In some embodiments, one or more of the features may be determined by measurement of Hounsfield units (HUs). For example, an intensity feature may be determined by measuring a HU of an imaging unit (e.g., a pixel or a voxel) of an image.

In some embodiments, the plurality of non-confounding PCAT features 110 may be selected at least in-part based upon a plurality of CCTA PCAT features 523 identified from the one or more CCTA images 502 to improve selection of relevant features. In some embodiments, the plurality of CCTA PCAT features 523 are extracted from voxels within one or more binary masks in the one or more CCTA images 502 (e.g., CCTA multiplanar reformation (MPR) images, CCTA axial-disk images, and CTCS axial-disk images). In some embodiments, the plurality of CCTA PCAT features 523 may be extracted in 3 categories: intensity features, traditional morphology features, and texture features. The intensity features may include histogram related features, such as minimum, mean, standard deviation, median, maximum value, skewness, kurtosis, entropy, potentially large bin histograms within fat region, and/or the like. The traditional morphology features may comprise a volume, shape, extent, and/or the like. The texture features may comprise a Gray-Level Co-Occurrence Matrix (GLCM), a Gray Level Dependence Matrix (GLDM), a Gray Level Run Length Matrix (GLRLM), a Neighborhood Grey-Tone Difference Matrix (NGTDM), and/or the like.

Because the extraction of the plurality of CCTA PCAT features 523 from the one or more CCTA images 502 may be more established, the identification of the plurality of non-confounding PCAT features 110 based upon the plurality of CCTA PCAT features 523 may be beneficial. For example, in some embodiments one or more of the plurality of non-confounding PCAT features 110 may be selected by a comparison 524 that determines an association to a corresponding one of the plurality of CCTA PCAT features 523 extracted from the automatically segmented CCTA PCAT 508 and/or assessments (e.g., high risk plaques (HRPs) and obstructive Fractional flow reserve derived from coronary CT angiography (FFRCT)) with high-risk atherosclerosis. In some embodiments, hierarchically clustered heatmaps may be used to compare the plurality of non-confounding PCAT features 110 to the plurality of CCTA PCAT features 523. The comparison may be used to select features, optimize computational enhancements, retool feature calculations, and rank order features for feature reduction using information gain. In some embodiments, a univariate logistic regression may be used to determine an ability of features to discriminate MACE and no-MACE.

In some additional embodiments, the plurality of confounding PCAT features 510 may be modified to generate adjusted PCAT features 522 that account for iodine confounds within the one or more CCTA images 502. The amount of iodine in PCAT will depend in-part upon a time since injection and/or obstructive disease in territories. Therefore, in some such embodiments, the automatically segmented CCTP PCAT 506 may be used to calculate potential iodine confounds 514. In some embodiments, the potential iodine confounds 514 (e.g., especially due to obstructive disease) may be calculated by analyzing HU and texture features at various time points in the one or more dynamic CCTP images. The potential iodine confounds 514 can be used to modify the plurality of confounding PCAT features 510 to generate the plurality of adjusted PCAT features 522, which can further improve feature selection from the automatically segmented PCAT 108.

The plurality of non-confounding PCAT features 110 are provided to a regression model 112 that is configured to utilize the plurality of non-confounding PCAT features 110 to generate a MACE risk score 116 that is indicative of a likelihood that a patient will have a MACE. Because the plurality of non-confounding PCAT features 110 do not suffer from iodine confoundment, the disclosed MACE assessment apparatus 515 is able to provide accurate prediction of a MACE.

FIG. 6 illustrates an exemplary ROC curve 600 comparing the disclosed method for MACE prediction with other methods for MACE prediction. The ROC curve 600 curve plots a true positive rate (TPR) along the y-axis and a false positive rate (FPR) along the x-axis.

The ROC curve 600 includes a first curve 302 corresponding to MACE prediction based upon an Agatston score, a second curve 602 corresponding to MACE prediction based upon a combination of an Agatston score and confounding PCAT features extracted from CCTA images, and a third curve 604 corresponding to MACE prediction based upon a combination of an Agatston score and non-confounding PCAT features extracted from CTCS images. The second curve 602 and the third curve 604 were each generated using 8 PCAT features.

As can be seen by comparison of the first curve 302 with the second curve 602 and the third curve 604, the inclusion of PCAT features significantly improves area under curves (AUCs). As can be seen by further comparison of the second curve 602 and the third curve 604, the use of non-confounding PCAT features extracted from CTCS images provides for improved results over the use of confounding PCAT features extracted from CCTA images. It was appreciated that the inclusion of an Agatston score improves the AUCs of PCAT features by approximately 0.02 for both CTCS images and CCTA images. It was also appreciated that without an Agatston score, the non-confounding PCAT features extracted from CTCS still outperformed results obtained using confounding PCAT features extracted from CCTA images.

FIG. 7A illustrates a graph 700 showing some exemplary Hounsfield unit (HU) values for a patient with a MACE and for a patient without a MACE.

As shown in graph 700, the HU values are averaged over three coronary arteries for a patient with a MACE and for a patient without a MACE. The HU values 702 for the three coronary arteries in CTCS have a lower p-value than the HU values 704 for the three coronary arteries in CCTA. For example, the HU values 702 for the three coronary arteries in CTCS have a p-value of 0.13, while the HU values for the three coronary arteries in CCTA have a p-value of 0.60. The lower HU values 702 for the three coronary arteries in CTCS indicates more accurate prognosis of MACE from CTCS images.

FIG. 7B illustrates a graph 706 showing some exemplary PCAT volumes for a patient with a MACE and for a patient without a MACE.

As shown in graph 706, the PCAT volumes 708 for CCTA images have a relatively high PCAT volume (p-value of 0.02) in comparison to the PCAT volumes 712 for CTCS images (p-value of 0.03). However, upon registration of CCTA images to a thick slice of CTCS images, the PCAT volumes 710 for CCTA images match well with the PCAT volumes 712 for CTCS images.

FIGS. 8A-8E illustrate a series of images that illustrate a comparison of artifacts between CTCS and CCTA images.

Figures 8A, 8B, 8C, 8D, 8E:
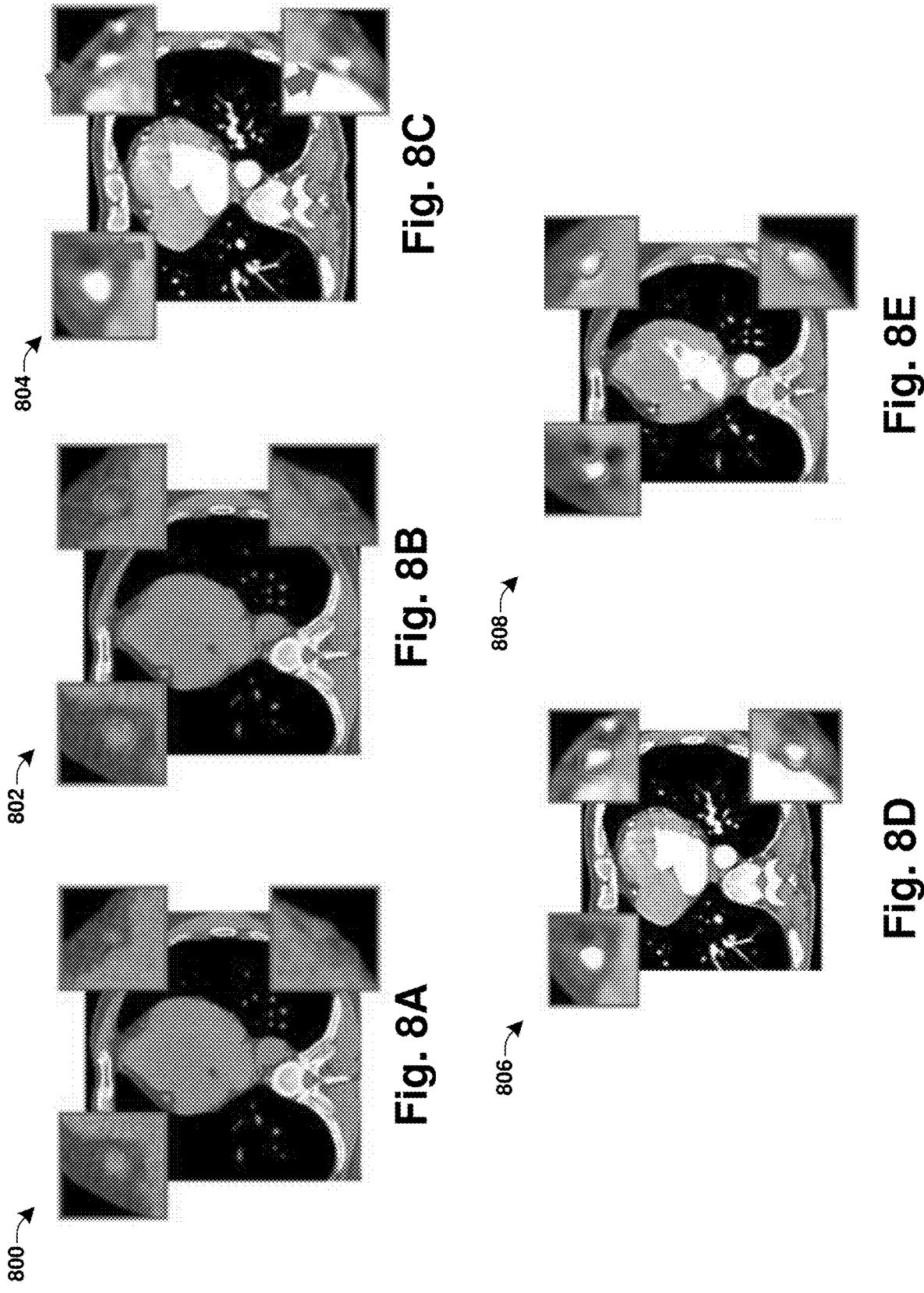
FIGS. 8A-8E illustrate a series of images that illustrate a comparison of artifacts between computed tomography calcium score (CTCS) and cardiac computed tomography angiography images (CCTA) images.

FIG. 8A illustrates a CTCS image 800 without segmentation. FIG. 8B illustrates a CTCS image 802 with segmentation. FIG. 8C illustrates a CCTA image without segmentation 804. FIG. 8D illustrates a CCTA image with segmentation 806. FIG. 8E illustrates a CCTA image 808 corresponding to CTCS image 802 following registration. The CCTA images 804-808 shown in FIGS. 8C-8E illustrate artifacts (e.g., streaking artifacts) that would affect extracted PCAT features. Such artifacts are absent from the CTCS images 800-802 of FIGS. 8A-8B, thereby indicating that CTCS images 800-802 are devoid of confounding factors such as artifacts and therefore are able to provide for a more accurate prediction of a prognosis (e.g., MACE).

FIGS. 9A-9E illustrate some exemplary comparisons of manually segmented PCAT and automatically segmented PCAT from CTCS images.

Figures 9A, 9B, 9C, 9D, 9E:
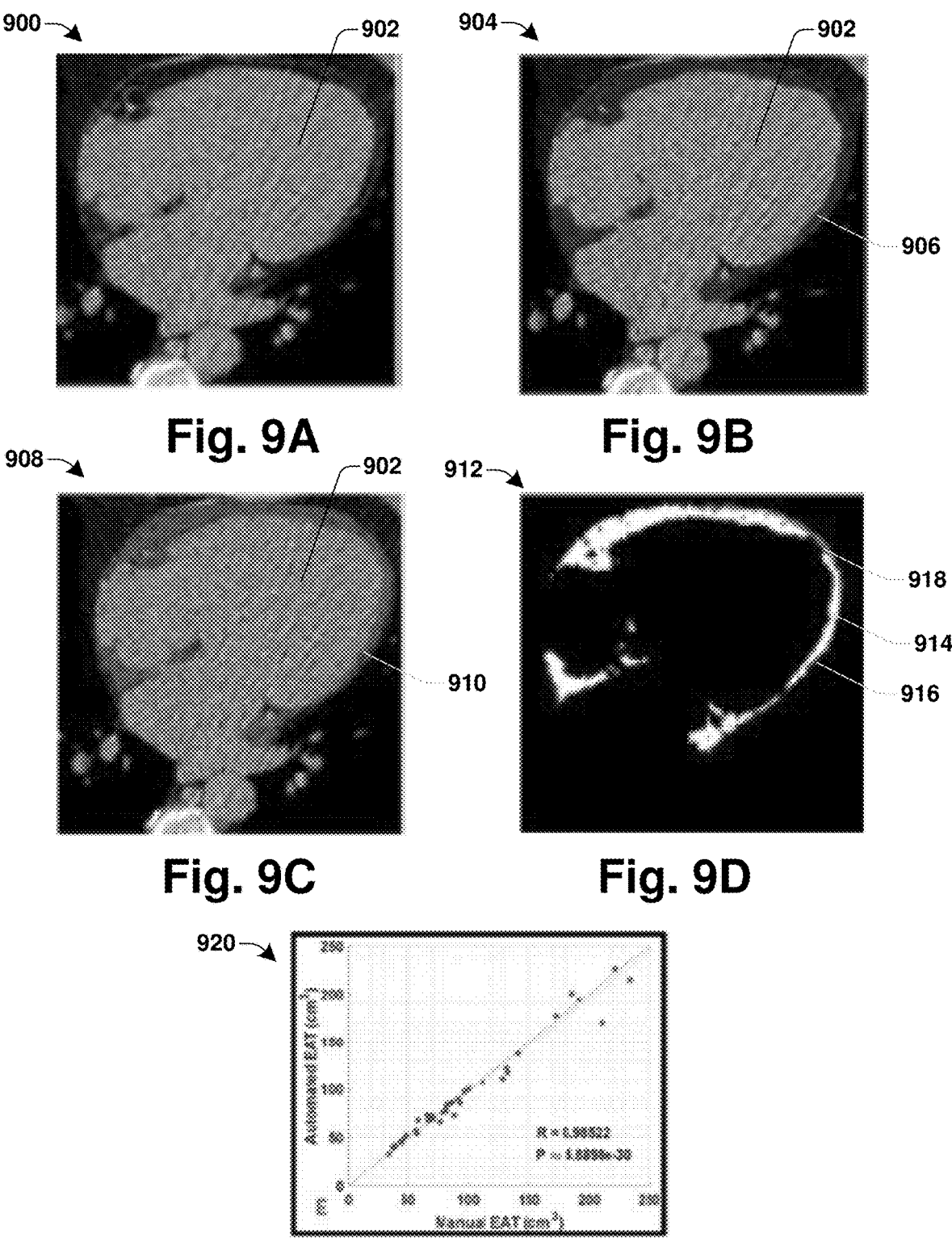
FIGS. 9A-9E illustrate some exemplary comparisons of manually segmented PCAT and automatically segmented PCAT from CTCS images.

FIG. 9A illustrates some embodiments of an axial CTCS image 900 of a heart 902 without segmentation.

FIG. 9B illustrates some embodiments of an axial CTCS image 904 of the heart 902 with a manually segmented PCAT 906 shown in blue. The manually segmented PCAT 906 is arranged along outer edges of the heart 902.

FIG. 9C illustrates some embodiments of the axial CTCS image 908 of the heart 902 with an automatically segmented PCAT 910 shown in red. The automatically segmented PCAT 910 is arranged along outer edges of the heart 902.

FIG. 9D illustrates some embodiments of the axial CTCS image 912 of a region of PCAT generated from an overlay of the manually segmented PCAT (e.g., 906 of FIG. 9B) and the automatically segmented PCAT (e.g., 910 of FIG. 9C). The overlapping regions 914 are shown in white, the regions 916 that are within the manually segmented PCAT but not the automatically segmented PCAT are shown in blue, and the regions 918 that are within the automatically segmented PCAT but not the manually segmented PCAT are shown in red. As can be seen in FIG. 9D, good agreement is present between the manually segmented PCAT and the automatically segmented PCAT.

FIG. 9E illustrates some embodiments of a graph 920 showing epicardial adipose tissue (EAT) volumes for manually segmented PCAT and automatically segmented PCAT. The graph 920 shows good agreement between the EAT volumes for manually segmented PCAT (shown along the x-axis) and automatically segmented PCAT (shown along the y-axis). For example, the graph 920 shows an R value of 0.98522 and a p-value of 5.8998e-30.

Figure 10:
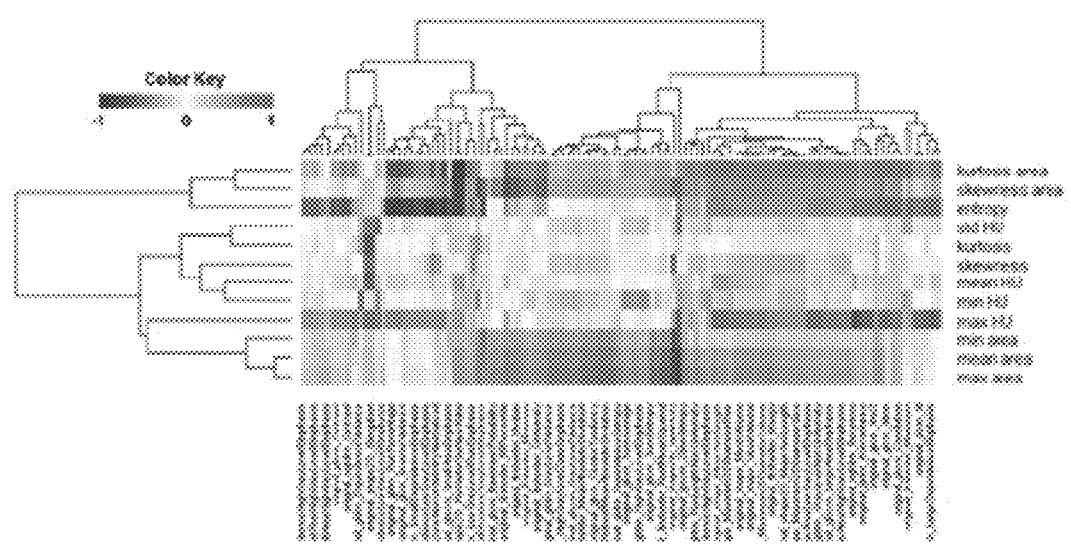
FIG. 10 illustrates an exemplary correlation heatmap comparing PCAT features extracted from CTCS and CCTA images.

FIG. 10 illustrates an exemplary correlation heatmap 1000 comparing PCAT features extracted from CTCS and CCTA images.

The correlation heatmap 1000 illustrates the exemplary CCTA features along the x-axis and the exemplary CTCS features along the y-axis. Spearman correlation coefficients are displaced with features hierarchically clustered. The correlation heatmap 1000 shows positive correlations with varying degrees of red. For example, a darker red corresponds to a stronger positive correlation than a light red. The correlation heatmap 1000 also shows negative correlations with varying degrees of blue. For example, a darker blue corresponds to a stronger negative correlation than a light blue.

As can be seen by the correlation heatmap 1000, some of the exemplary CTCS features show strong positive correlations with the exemplary CCTA features (e.g., shown in red), while other exemplary CTCS features show a strong negative correlation with the exemplary CCTA features (e.g., shown in blue). Therefore, the correlation heatmap 1000 shows that there is a discriminability between CCTA features and CTCS features, such that the CCTA features can be used to aid in feature selection for CTCS images.

Figure 11:
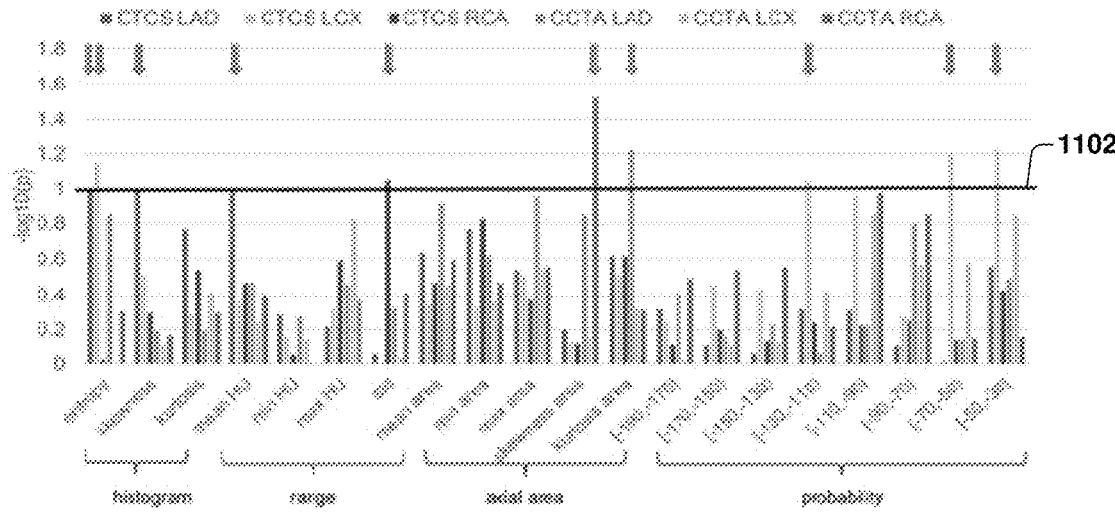
FIG. 11 illustrates a graph showing an exemplary statistical analysis of PCAT features extracted from CTCS and CCTA images.

FIG. 11 illustrates a graph 1100 showing an exemplary statistical analysis of PCAT features extracted from CTCS and CCTA images.

The graph 1100 illustrates 20 PCAT features along the x-axis. The 20 PCAT features were extracted from 3 coronary arteries in one or more CTCS images and in one or more CCTA images. The 20 PCAT features include 4 histogram shape features, 4 histogram range features, 5 PCAT area features in axial slices, and 7 probability features in range of HU values. P-values for the 20 PCAT features are shown along the y-axis. In some embodiments, the p-values for the 20 PCAT features may be obtained for the features using Univariate logistic regression on MACE groups and groups without MACE.

Features deemed to be discriminant are shown as extending to and/or above line 1102. Of the 20 PCAT features extracted from the one or more CTCS images, 8 features were deemed discriminant (e.g., entropy of CTCS LAD, entropy of CTCS LCX, skewness of CTCS LAD, mean HU of CTCS LAD, standard deviation (std) of CTCS LAD, etc.) Of the 20 PCAT features extracted from the one or more CCTA images, only 2 features were deemed discriminant (e.g., skewness area of CCTA RCE and kurtosis area of CCTA LAD). The larger number of discriminant PCAT features associated with CTCS images indicates that the PCAT features associated with CTCS images are more likely to lead to accurate prognosis of a MACE within a patient.

Figure 12:
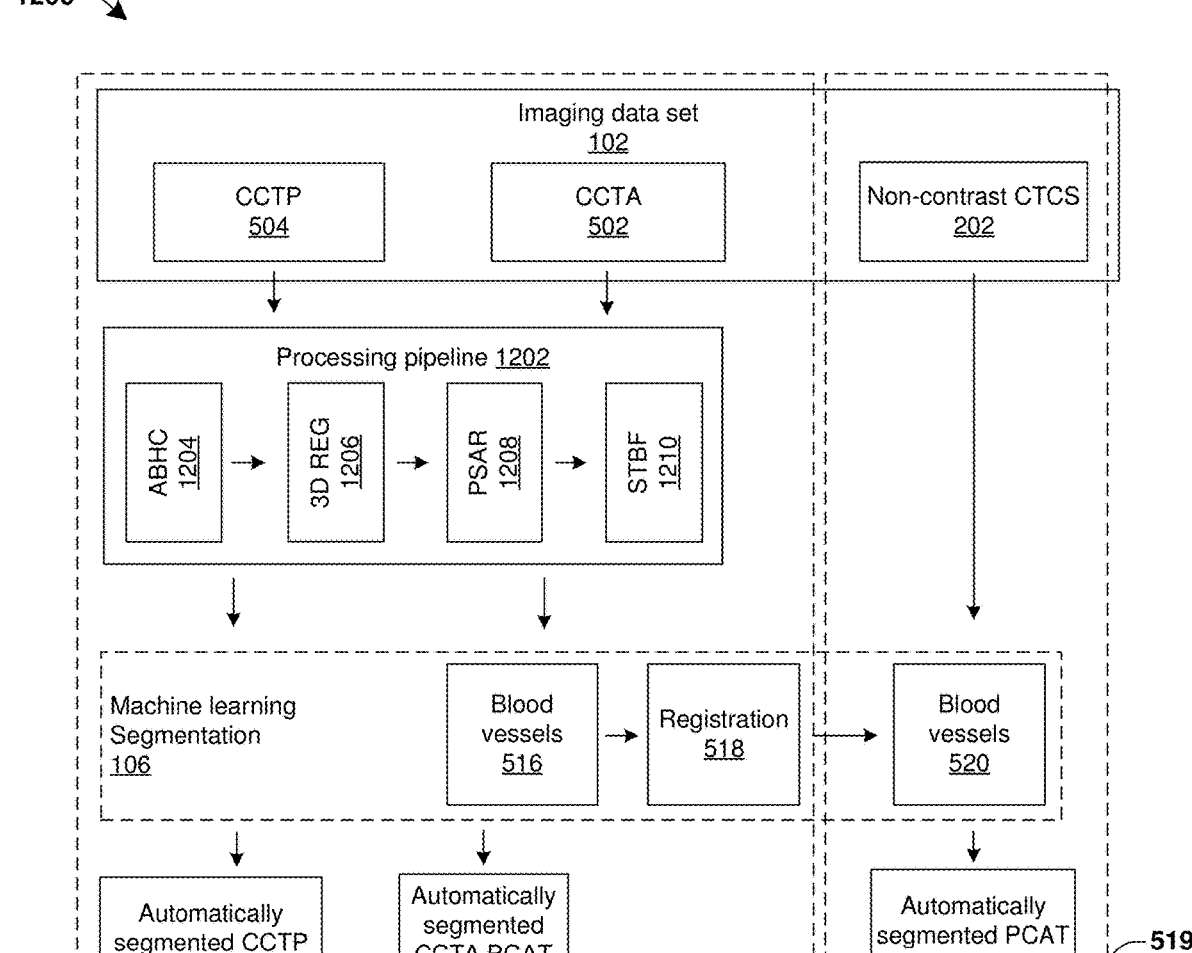
FIG. 12 illustrates a block diagram corresponding to some additional embodiments of a MACE assessment apparatus configured to determine a likelihood of a MACE using non-confounding PCAT features.

FIG. 12 illustrates a block diagram corresponding to some additional embodiments of a MACE assessment apparatus 1200 configured to determine a likelihood of a MACE using non-confounding PCAT features.

The MACE assessment apparatus 1200 comprises an imaging data set 102. In some embodiments the imaging data set 102 comprises one or more non-contrast CTCS images 202. In some additional embodiments, the imaging data set 102 may further comprise one or more CCTP images 504 and one or more CCTA images 502. The MACE assessment apparatus 1200 is configured to utilize the one or more CCTP images 504 to determine iodine confounds in one or more CCTA images 502 so as to improve identification of PCAT features within the one or more non-contrast CTCS images 202 during training.

In some embodiments, the MACE assessment apparatus 1200 comprises a machine learning segmentation tool 106 that is configured to identify PCAT within the one or more CCTP images 504 and the one or more CCTA images 502. In some embodiments, coronary arteries are segmented from the peak enhancement scan semi-automatically. In some embodiments, PCAT regions are defined as regions with radius equal to the coronary artery diameter. In some embodiments, PCAT regions are defined as voxels in range of −190 HU to −30 HU.

In some embodiments, the MACE assessment apparatus 1200 may comprise a blood flow perfusion tool 512 configured to estimate PCAT perfusion parameters (e.g., mean blood flow, mean transit time, delay, extraction fraction, and peak contrast) based upon the one or more CCTP images 504. In some embodiments, before blood flow computation, super-voxel clustering may be performed to reduce noise, improve the quality of resultant flow maps, and greatly accelerate computation times. In some embodiments, for blood flow computation, a user may define a size and location of a ROI from which to obtain the arterial input function (e.g., in the LV cavity or aorta). In some embodiments, the blood flow perfusion tool 512 may output perfusion images for the CT volume, or sub-volume. From the perfusion images, blood flow perfusion is assessed and changes in the confounding PCAT features 510 with iodine infusion may be made to form adjusted PCAT features 522. In some embodiments, HU and texture features may be analyzed at various time points in dynamic CCTP to determine potential iodine confounds, especially due to obstructive disease.

It has been appreciated that the one or more CCTP images 504 and the one or more CCTA images 502 and may suffer from confounding factors such as artifacts. To reduce such confounding factors, in some embodiments the MACE assessment apparatus 1200 may comprise a processing pipeline 1202 that is configured to perform one or more operations on the one or more CCTP images 504 and the one or more CCTA images 502 to reduce confounding factors. In some embodiments, the processing pipeline 1202 may comprise an automatic beam hardening correction (ABHC) element 1204, a 3D registration element 1206, a partial scan artifact reduction element 1208, and/or a spatio-temporal bilateral filtering element 1210.

In some embodiments, the ABHC element 1204 is configured to apply beam hardening correction to reduce beam hardening artifacts which can otherwise reduce Hounsfield unit (HU) values of PCAT and which may interfere with accurate and precise quantitative perfusion analysis. In some embodiments, the image-based ABHC algorithm automatically determines correction parameters for a beam hardening correction model and applies them to reduce artifacts in the image.

In some embodiments, the 3D registration element 1206 is configured to apply 3D registration to improve data quality by minimizing motion between image frames (e.g., at edges between the myocardium and ventricle blood pools or the myocardium and lung). The algorithm uses a nonrigid image transformation model to achieve high-quality registration. One example spatial transformation method is bicubic splines, but other transformation models can be used. Image volumes at each time point are registered to the image volume at peak left ventricle cavity enhancement using a gray-scale similarity measure. This time was found to provide strong contrast between the LV cavity, RV cavity, and myocardium. By registering to the same time point, this reduces the likelihood of "drift" during registration as compared to a sequential registration of adjacent image frames through time.

In some embodiments, the partial scan artifact reduction element 1208 is configured to apply an optional correction for partial scan acquisitions and reconstructions (180 degree+fan angle) which are known to introduce shading artifacts. To address this, the algorithm determines the correction by generating a virtual full scan image by averaging the full dynamic image sequence, denoted "FS" for full scan, and a corresponding partial scan by averaging partial scan images, denoted "PS", acquired at the same acquisition angle as the current image, denoted "I". The difference between FS and PS is the artifact correction. The corrected image, denoted "Ic" is generated by Ic=I+FS−PS.

In some embodiments, the spatio-temporal bilateral filtering element 1210 is configured to apply an edge-preserving 3D spatio-temporal filter to reduce the effect of fluctuations introduced by partial scan artifacts. The filter is applied to 4D data in two different steps. First, for any given temporal position, 3D non-linear diffusion filtration is performed in the spatial domain. Then, the filter operates on adjacent temporal positions.

FIG. 13 illustrates a flow diagram corresponding to some additional embodiments of a method 1300 of determining a likelihood of a MACE using non-confounding PCAT features.

At act 1302, an imaging data set is formed to comprise one or more CCTA images, one or more CCTP images, and one or more CTCS images of a patient.

At act 1304, the one or more CCTA images and the one or more CCTP images are processed to improve a quality of the images for subsequently segmentation. In some embodiments, the processing may comprise applying beam hardening correction to an image, at act 1306, to reduce beam hardening artifacts. In some embodiments, the processing may comprise performing 3D registration, at act 1308, to improve data quality by minimizing motion between image frames to reduce beam hardening artifacts. In some embodiments, the processing may comprise a correction for partial scan acquisitions and reconstructions, at act 1310. In some embodiments, the processing may comprise applying a spatio-temporal filter, at act 1312, to reduce the effects of fluctuations introduced by partial scan artifacts.

At act 1314, the one or more CCTA images, CCTP images, and CTCS images are segmented to identify pericoronary adipose tissue (PCAT).

At act 1316, the automatically segmented PCAT is stored within an electronic memory.

At act 1318, a blood flow is computed in the PCAT of the one or more CCTP images.

At act 1320, blood flow and/or iodine perfusion is assessed in PCAT of the one or more CCTP images from the PCAT blood flow. In some embodiments, iodine perfusion may be accounted using blood flow perfusion.

At act 1322, PCAT features are extracted from PCAT of CCTA images taking into account blood flow and/or iodine perfusion. In some embodiments, the blood flow and/or iodine perfusion may be accounted for during extraction of the PCAT features. In some embodiments, the PCAT features may be analyzed at different points in time to determine potential iodine confounds in the PCAT. For example, PCAT features at various time points may be analyzed in dynamic cardiac CT perfusion (CCTP) exams to identify potential iodine confounds.

At act 1324, non-confounding PCAT features are extracted from automatically segmented PCAT of CTCS images using PCAT features extracted from PCAT of CCTA images. In some embodiments, the non-confounding PCAT features may be extracted by associating CTCS PCAT features to established PCAT features from CCTA.

At act 1326, an Agatston score associated with the patient is determined.

At act 1328, a major adverse cardiovascular event (MACE) risk prediction is generated using extracted PCAT features and/or the Agatston score. In some embodiments, the MACE risk prediction may be generated using a Cox-proportional hazard time-to-event model.

Figure 14:
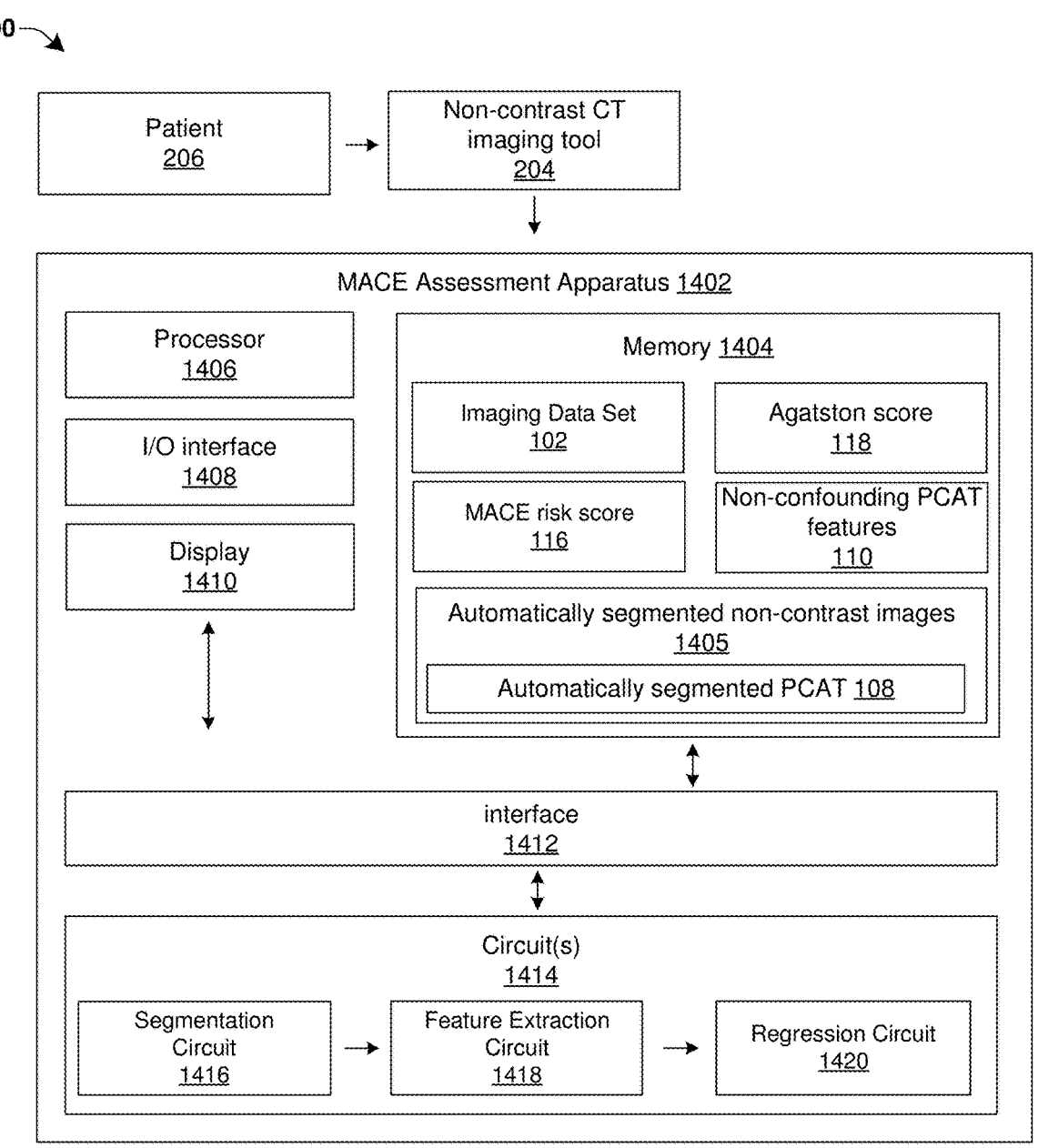
FIG. 14 illustrates a block diagram of some embodiments of an apparatus configured to determine a likelihood of a MACE using non-confounding PCAT features.

FIG. 14 illustrates a block diagram of some embodiments of an apparatus 1400 configured to determine a likelihood of a MACE using non-confounding PCAT features.

The apparatus 1400 comprises a MACE assessment apparatus 1402. The MACE assessment apparatus 1402 is coupled to a non-contrast CT imaging tool 204 that is configured to generate one or more non-contrast images (e.g., CTCS images) of a patient 206. In some embodiments, the non-contrast CT imaging tool 204 may comprise a low-dose CT scanner.

The MACE assessment apparatus 1402 comprises a processor 1406 and a memory 1404. The processor 1406 can, in various embodiments, comprise circuitry such as, but not limited to, one or more single-core or multi-core processors. The processor 1406 can include any combination of general-purpose processors and dedicated processors (e.g., graphics processors, application processors, etc.). The processor(s) 1406 can be coupled with and/or can comprise memory (e.g., memory 1404) or storage and can be configured to execute instructions stored in the memory 1404 or storage to enable various apparatus, applications, or operating systems to perform operations and/or methods discussed herein.

Memory 1404 can be further configured to store an imaging data set 102 comprising the one or more digitized images (e.g., non-contrast digitized images) obtained by the non-contrast CT imaging tool 204. The one or more digitized images may comprise a plurality of pixels, each pixel having an associated intensity. In some additional embodiments, the one or more digitized images may be stored in the memory 1404 as one or more training sets of digitized images for training a classifier and/or one or more validation sets (e.g., test sets) of digitized images.

The MACE assessment apparatus 1402 also comprises an input/output (I/O) interface 1408 (e.g., associated with one or more I/O devices), a display 1410, one or more circuits 1414, and an interface 1412 that connects the processor 1406, the memory 1404, the I/O interface 1408, the display 1410, and the one or more circuits 1414. The I/O interface 1408 can be configured to transfer data between the memory 1404, the processor 1406, the one or more circuits 1414, and external devices (e.g., non-contrast CT imaging tool 204).

In some embodiments, the one or more circuits 1414 may comprise hardware components. In other embodiments, the one or more circuits 1414 may comprise software components. The one or more circuits 1414 can comprise a segmentation circuit 1416 (e.g., a deep learning circuit) configured to perform a segmentation operation on one or more digitized images within the imaging data set 102 to identify segmented parts of a blood vessel (e.g., a lumen, a calcification lesion, etc.). In some additional embodiments, the segmentation circuit 1416 may be configured to segment the one or more digitized images to generate one or more automatically segmented non-contrast images 1405 (e.g., binary masks), which may be stored in the memory 1404. The one or more automatically segmented non-contrast images 1405 may comprise automatically segmented PCAT 108.

In some additional embodiments, the one or more circuits 1414 may further comprise feature extraction circuit 1418 configured to extract a plurality of non-confounding PCAT features 110 from the automatically segmented PCAT 108. The plurality of non-confounding PCAT features 110 may be stored in the memory 1404.

In some embodiments, the one or more circuits 1414 may further comprise a regression circuit 1420 configured to operate a regression model (e.g., a Cox-proportional Hazard model) upon the plurality of non-confounding PCAT features 110 to generate a MACE risk score 116.

Therefore, the present disclosure relates to a method and associated apparatus that utilizes non-confounding PCAT features extracted from pericoronary adipose tissue (PCAT) within digitized images (e.g., low-dose computed tomography (CT) calcium score (CTCS) images) to predict major adverse cardiovascular events (MACE).

In some embodiments, the present disclosure relates to a method. The method includes accessing automatically segmented pericoronary adipose tissue (PCAT) corresponding to a patient from within an electronic memory; generating a plurality of non-confounding PCAT features by measuring values of Hounsfield units for an imaging unit within the PCAT, the measured values of the Hounsfield units being predominately free of iodine confounding and artifacts; and providing the plurality of non-confounding PCAT features to a regression model, the regression model being configured to generate a prognosis for the patient using the plurality of non-confounding PCAT features.

In other embodiments, the present disclosure relates to a non-transitory computer-readable medium storing computer-executable instructions that, when executed, cause a processor to perform operations, including automatically segmenting one or more computed tomography calcium score (CTCS) images and identify automatically segmented pericoronary adipose tissue (PCAT) within a patient; extracting a plurality of non-confounding PCAT features from the automatically segmented PCAT, measurement of the plurality of non-confounding PCAT features being predominately free of iodine confounding and artifacts; and providing the plurality of non-confounding PCAT features to a regression model, the regression model being configured to generate a major adverse cardiovascular event (MACE) risk score for the patient using the plurality of non-confounding PCAT features.

In yet other embodiments, the present disclosure relates to an assessment apparatus. The assessment apparatus includes a memory configured to store one or more automatically segmented non-contrast images, the one or more automatically segmented non-contrast images identifying automatically segmented pericoronary adipose tissue (PCAT) within computed tomography calcium score (CTCS) images of a patient; a feature extraction circuit configured to extract a plurality of non-confounding PCAT features from the automatically segmented PCAT, wherein the plurality of non-confounding PCAT features are predominately free of iodine confounding and artifacts; and a regression circuit configured to generate a major adverse cardiovascular event (MACE) risk score for the patient using the plurality of non-confounding PCAT features.

Examples herein can include subject matter such as an apparatus, including a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system according to embodiments and examples described. References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and vola-tile media. Non-volatile media may include, for example, optical disks, magnetic disks, tapes, and other media. Vola-tile media may include, for example, semiconductor memo-ries, dynamic memory, and other media. Common forms of a computer-readable storage device may include, but are not limited to, a floppy disk, a flexible disk, a hard disk, a magnetic tape, other magnetic medium, an application spe-cific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software con-trolled microprocessor, a discrete logic (e.g., ASIC), an analog circuit, a digital circuit, a programmed logic device, a memory device containing instructions, and other physical devices. A circuit may include one or more gates, combi-nations of gates, or other circuit components. Where mul-tiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combi-nation of components or methodologies for purposes of describing the systems, methods, and other embodiments described herein. Therefore, the invention is not limited to the specific details, the representative apparatus, and illus-trative examples shown and described. Thus, this application is intended to embrace alterations, modifications, and varia-tions that fall within the scope of the appended claims.

What is claimed is:

1. A non-transitory computer-readable medium storing computer-executable instructions that, when executed, cause a processor to perform operations, comprising:

automatically segmenting one or more computed tomog-raphy calcium score (CTCS) images of a patient and identifying automatically segmented pericoronary adi-pose tissue (PCAT) within the CTCS images of the patient;

extracting a plurality of non-confounding PCAT features from the automatically segmented PCAT, wherein mea-surement of the plurality of non-confounding PCAT features is predominantly free of iodine confounding and artifacts; and providing the plurality of non-confounding PCAT fea-tures to a regression model, the regression model being configured to generate a major adverse cardiovascular event (MACE) risk score for the patient using the plurality of non-confounding PCAT features.

2. The non-transitory computer-readable medium of claim 1, wherein the operations further comprise:

providing an Agatston score to the regression model, wherein the regression model is configured to generate the MACE risk score using the plurality of non-con-founding PCAT features and the Agatston score.

3. The non-transitory computer-readable medium of claim 1, wherein extracting the plurality of non-confounding PCAT features includes measuring values of Hounsfield units for a pixel or a voxel within the automatically seg-mented PCAT.

4. The non-transitory computer-readable medium of claim 1, wherein the plurality of non-confounding PCAT features comprise intensity features, morphology features, and tex-ture features.

5. The non-transitory computer-readable medium of claim 1, wherein the operations further comprise:

automatically segmenting one or more cardiac computed tomography perfusion (CCTP) images to identify auto-matically segmented CCTP PCAT;

determining potential iodine confounds from the auto-matically segmented CCTP PCAT;

automatically segmenting one or more coronary com-puted tomography angiogram (CCTA) images to iden-tify automatically segmented CCTA PCAT;

generating a plurality of CCTA PCAT features from the automatically segmented CCTA PCAT, wherein the plurality of CCTA PCAT features are modified based upon the potential iodine confounds; and utilizing the plurality of CCTA PCAT features to aid in selection of the plurality of non-confounding PCAT features.

6. The non-transitory computer-readable medium of claim 1, wherein the operations further comprise:

automatically segmenting one or more CCTA images to identify CCTA PCAT and coronary arteries; and registering the coronary arteries to the one or more CTCS images.

7. An assessment apparatus, comprising:

a memory configured to store one or more automatically segmented non-contrast images, the one or more auto-matically segmented non-contrast images identifying automatically segmented pericoronary adipose tissue (PCAT) within computed tomography calcium score (CTCS) images of a patient;

a feature extraction circuit configured to extract a plurality of non-confounding PCAT features from the automati-cally segmented PCAT, wherein the plurality of non-confounding PCAT features are predominately free of iodine confounding and artifacts; and a regression circuit configured to generate a major adverse cardiovascular event (MACE) risk score for the patient using the plurality of non-confounding PCAT features.

8. The assessment apparatus of claim 7, wherein the regression circuit is configured to generate a MACE risk prediction using the plurality of non-confounding PCAT features and an Agatston score of the patient.

9. The assessment apparatus of claim 7, wherein extracting the plurality of non-confounding PCAT features includes measuring values of Hounsfield units for a pixel or a voxel within the automatically segmented PCAT.

10. The assessment apparatus of claim 7, wherein the plurality of non-confounding PCAT features comprise intensity features, morphology features, and texture features.

11. The assessment apparatus of claim 7, wherein the feature extraction circuit is configured to utilize a plurality of CCTA PCAT features extracted from automatically segmented CCTA PCAT within one or more coronary computed tomography angiogram (CCTA) images to aid in selection of the plurality of non-confounding PCAT features.

12. A method, comprising:

automatically segmenting one or more computed tomography calcium score (CTCS) images of a patient and identifying automatically segmented pericoronary adipose tissue (PCAT) within the CTCS images of the patient;

extracting a plurality of non-confounding PCAT features from the automatically segmented PCAT, wherein measurement of the plurality of non-confounding PCAT features is predominantly free of iodine confounding and artifacts; and providing the plurality of non-confounding PCAT features to a regression model, the regression model being configured to generate a major adverse cardiovascular event (MACE) risk score for the patient using the plurality of non-confounding PCAT features.

13. The method of claim 12, further comprising:

providing an Agatston score to the regression model, wherein the regression model is configured to generate the MACE risk score using the plurality of non-confounding PCAT features and the Agatston score.

14. The method of claim 12, wherein extracting the plurality of non-confounding PCAT features includes measuring values of Hounsfield units for a pixel or a voxel within the automatically segmented PCAT.

15. The method of claim 12, wherein the plurality of non-confounding PCAT features comprise intensity features, morphology features, and texture features.

16. The method of claim 12, further comprising:

automatically segmenting one or more cardiac computed tomography perfusion (CCTP) images to identify automatically segmented CCTP PCAT;

determining potential iodine confounds from the automatically segmented CCTP PCAT;

automatically segmenting one or more coronary computed tomography angiogram (CCTA) images to identify automatically segmented CCTA PCAT;

generating a plurality of CCTA PCAT features from the automatically segmented CCTA PCAT, wherein the plurality of CCTA PCAT features are modified based upon the potential iodine confounds; and utilizing the plurality of CCTA PCAT features to aid in selection of the plurality of non-confounding PCAT features.

17. The method of claim 12, further comprise:

automatically segmenting one or more CCTA images to identify CCTA PCAT and coronary arteries; and registering the coronary arteries to the one or more CTCS images.

* * * * *